United States Patent [19]

Waizmann

[11] Patent Number: 5,060,572
[45] Date of Patent: Oct. 29, 1991

[54] CONTINUOUS DRIER ON ROTARY OFFSET PRINTING PRESSES AND OPERATION OF SUCH A DRIER DURING THE PRINTING AND CYLINDER WASHING PROCESSES WITH THE WEB RUNNING

[75] Inventor: Franz Waizmann, Gessertshausen, Fed. Rep. of Germany

[73] Assignee: Baldwin-Gegenheimer GmbH, Fed. Rep. of Germany

[21] Appl. No.: 470,139

[22] Filed: Jan. 25, 1990

[30] Foreign Application Priority Data

Jan. 25, 1989 [DE] Fed. Rep. of Germany ....... 3902180
Nov. 27, 1989 [DE] Fed. Rep. of Germany ....... 3939190

[51] Int. Cl.$^5$ .......................... B41F 23/04; F23N 5/24
[52] U.S. Cl. .................. 101/424.1; 101/484; 101/488; 34/23; 34/48; 250/343; 431/76; 432/8; 432/37
[58] Field of Search .............. 101/424.1, 484, 488, 101/487; 34/23, 36, 37, 155, 47, 48; 432/8, 23, 37; 250/343; 431/76

[56] References Cited

U.S. PATENT DOCUMENTS

| | | | |
|---|---|---|---|
| 3,566,091 | 2/1971 | Bay et al. ........................ | 432/37 X |
| 4,084,906 | 4/1978 | Bibbero ........................... | 250/343 X |
| 4,138,725 | 2/1979 | Ikemoto et al. .................. | 431/76 X |
| 4,147,500 | 4/1979 | Karlsoen ......................... | 431/76 X |
| 4,150,495 | 4/1979 | Stern ............................. | 101/424.1 X |
| 4,158,772 | 6/1979 | Reedy ............................ | 250/343 X |
| 4,330,260 | 5/1982 | Jorgensen et al. ............... | 431/76 X |
| 4,362,269 | 12/1982 | Rastogi et al. .................. | 431/76 X |
| 4,362,499 | 12/1982 | Nethery .......................... | 431/76 X |
| 4,520,265 | 5/1985 | Griggs et al. ................... | 250/343 X |
| 4,686,902 | 8/1987 | Allain et al. .................... | 101/425 X |

FOREIGN PATENT DOCUMENTS

| | | | |
|---|---|---|---|
| 49233 | 4/1982 | European Pat. Off. ......... | 101/424.1 |
| 2150259 | 4/1973 | Fed. Rep. of Germany ... | 101/424.1 |
| 39304 | 3/1980 | Japan ............................. | 101/424.1 |
| 679550 | 8/1979 | U.S.S.R. ......................... | 432/37 |
| 2073390 | 10/1981 | United Kingdom ............ | 101/424.1 |

Primary Examiner—Clifford D. Crowder
Attorney, Agent, or Firm—Christie, Parker & Hale

[57] ABSTRACT

A continuous drier for drying a printed web on web-fed rotary printing presses operates during ongoing printing and blanket washing processes with control of the gaseous and vaporous constituents of the ink, solvent, and burner gases. An infrared beam path is installed in the drier to measure concentrations of gas vapors in the drier by an extinction method. The continuous drier process is thus controlled according to the rate of evaporation of volatile constituents. The infrared extinction measurement yields spectral measurements of vapors released by the printing ink during the printing process, or of solvent constituents released during the blanket cleaning process, each according to their characteristic band position and intensity. During the transition from printing to blanket washing, the user obtains an instant picture, based on the band intensities, of the current vapor concentrations. Depending on the concentration limits, he can then adjust the flow, heating and ventilation settings within the drier system or selectively adjust solvent dosages. In conjunction with rapid control interventions or preprogrammed adjustments, this undelayed on-line measuring system prevents explosions in the drier. The system also allows the composition of the printing ink, with its varying application rates, to be controlled based on the measured extinction values. Similarly, the burner settings can be controlled via the CO and fuel gas bands in the drier.

33 Claims, 5 Drawing Sheets

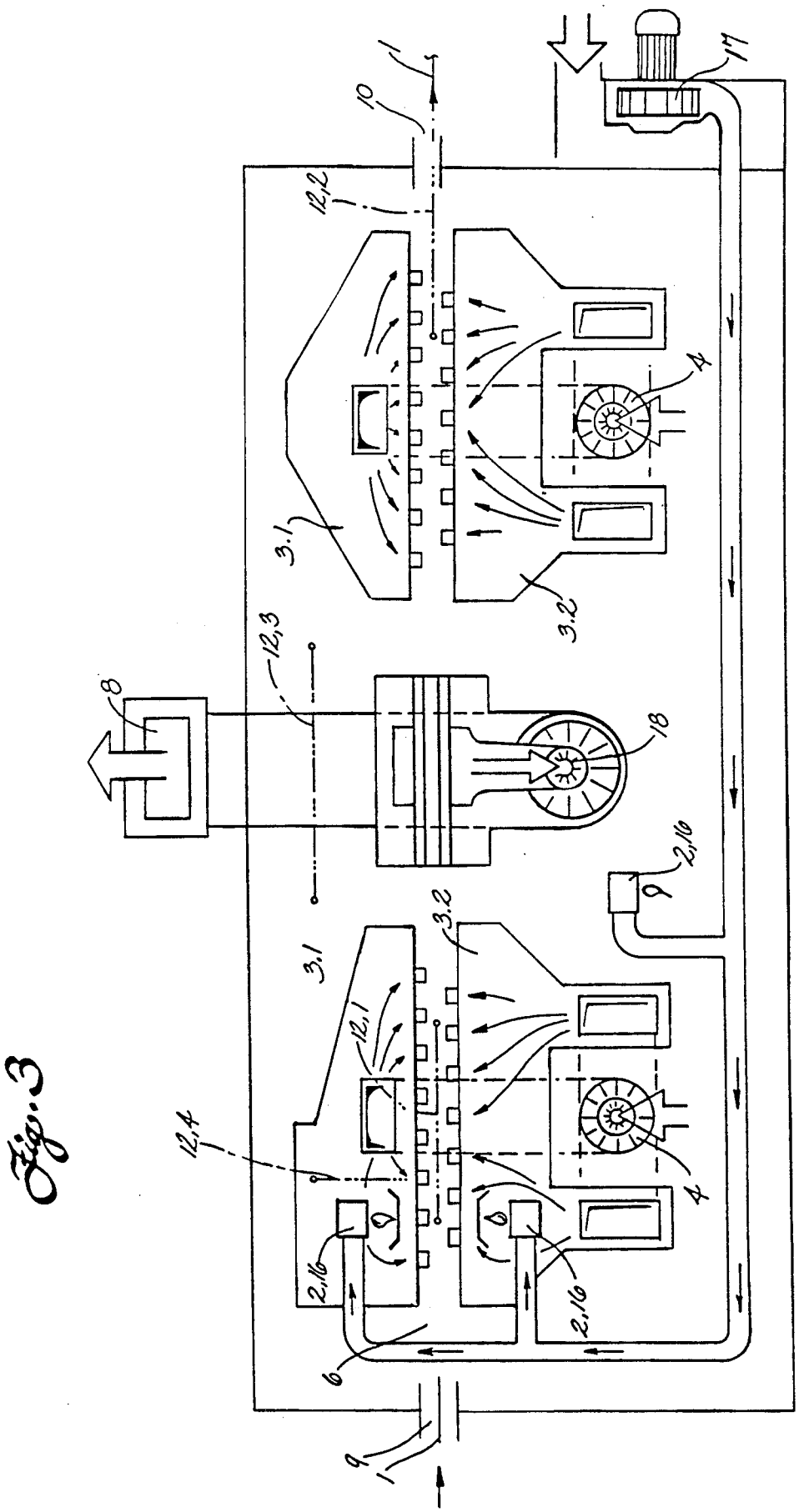

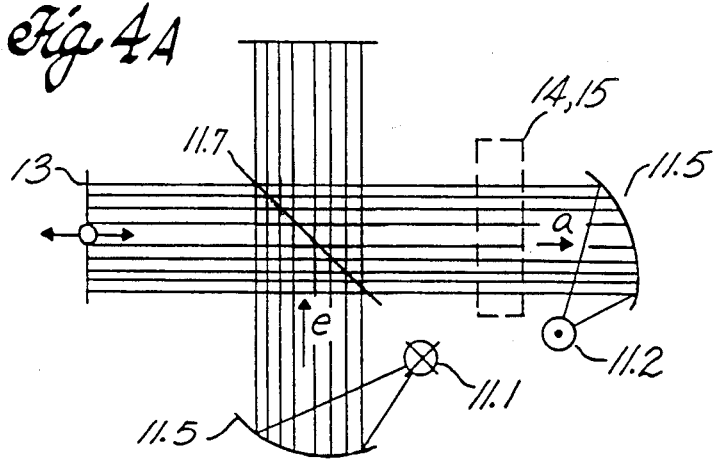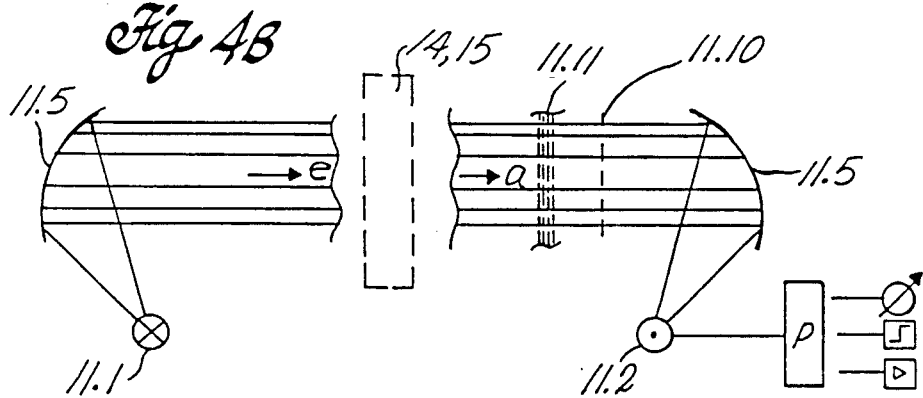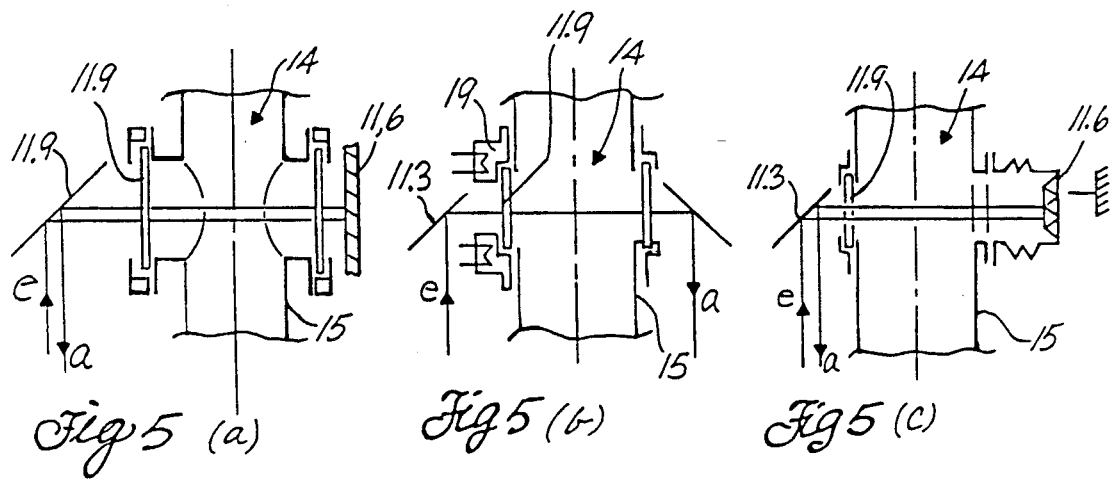

$E_{max} = \lg \dfrac{T_B}{T'}$

CONTINUOUS DRIER ON ROTARY OFFSET PRINTING PRESSES AND OPERATION OF SUCH A DRIER DURING THE PRINTING AND CYLINDER WASHING PROCESSES WITH THE WEB RUNNING

CROSS-REFERENCE TO RELATED APPLICATIONS AND CLAIM FOR PRIORITY

This application is based on, and claims priority from, an application first filed in Federal Republic of Germany on 25 Jan. 1989, under Ser. No. P 39 02 180.7, and an application first filed in Federal Republic of Germany on 27 Nov. 1989, under Ser. No. P 39 39 190.6. To the extent such prior applications may contain any additional information of assistance in the understanding and use of the invention claimed herein, they are hereby incorporated by reference.

FIELD OF THE INVENTION

This invention relates to a continuous drier on web-fed rotary printing presses and to the operation of such a continuous drier during printing and blanket washing with regard to the control of ink vapors, solvent vapors and burner gases.

BACKGROUND OF THE INVENTION

Such continuous driers are used in printing lines where a web is unwound from a roll, passes a plurality of printing units which apply patterns to it in due register, and runs through a thermally operating continuous drier before reaching a folding device where it is processed into the finished copies.

The basic features of continuous driers and their operation are set out in the "Safety Regulations for Printing and Paper Processing Machines" published by Carl Heymann Verlag KG, Order No. ZH/19, Oct. 1984. According to this publication, solvents or substances containing solvents which are introduced into a continuous drier may therein react with air to produce a potentially explosive mixture of solvent vapor and air. As a result of the installed unprotected heating systems, which heat the fresh and circulated air destined for the drying tunnel to a certain temperature, there is no gas-tight separation between the drying tunnel and the burner chamber. The manufacturer or operating company is required to specify a threshold temperature which is lower than the ignition temperature (refer to DIN 51794) and lower than the inflammation temperature at which combustion phenomena will result. According to the definition of unprotected heating systems, the temperature of the heated air flow will partially exceed the threshold temperature. Said threshold temperature has been fixed at 80% of the ignition temperature laid down in DIN 51794.

The inflammable substances are assigned a lower explosion concentration limit at which, after ignition, a flame independent of the ignition source will just cease to be able to propagate on its own. In the case of continuous driers with unprotected heating in the circulated air channel, it is assumed that the solvent vapor concentration immediately upstream of the unprotected heating system will not exceed 25% of the LEL threshold. In the event of an unknown solvent vapor concentration, the LEL of the solvent is assumed to be 20 g/m$^3$ for reference purposes.

As there exists a threshold temperature which must not be exceeded during continuous drier operation, the heating system for the continuous drier must be equipped with a temperature control system or at least with a temperature restricting device. Applicable rules and regulations also prescribe that the restriction of the solvent vapor concentration in the continuous drier should be monitored by a gas warning system which must reliably register any hazardous quantities of such vapors that might constitute a potentially explosive atmosphere. The sensor of this gas warning system should provide at least five measurements per minute for each measuring point.

The problem exists that these officially prescribed gas warning systems merely provide measured values at given intervals and from a so-called representative point, so that sudden changes in concentration levels or changes in the composition of the vaporizing materials applied to the web cannot be adequately picked up. In addition, the control of the drier process is not based on the actual gas or vapor concentration but on a temperature program for the heating system, which, in the case of unprotected heaters, is derived from ignition flash points.

To monitor the solvent vapors in the continuous drier it is standard practice to install a flame-ionization detector (FID). German Patent No. 2150259 B2 discloses a gas-measuring system attached to an extraction funnel on a low-pressure drier with which the gas proportion of toluene in the air can be determined.

The design of known infrared measuring systems may vary greatly, depending on the individual application. The device designed in accordance with European Patent No. 0123458 has a small test chamber which can be filled with the gas to be measured. Filters are installed to generate radiation in the absorption wavelength area. The invention presented in German Publication No. 211835 operates with interference filters for the absorption bands of the gas constituents to be analyzed. By using laser-induced radiation in a system which, through its very nature, is spectrally restricted to one absorption range, this design is only useful for a single constituent; at least it will require sophisticated equipment to provide tuning facilities for application throughout a wider radiation spectrum. An absorption system using a laser beam is described in U.S. Pat. No. 4,475,816.

Inventions using measuring chambers and sampling systems have the disadvantage that the gas constituent measurement will not yield representative values and is also too slow. FID systems provide delayed indications. Known infrared measuring devices are based on standard components and physical processes which allow the user to resolve a large range of measurement tasks; however, the infrared measuring instruments known for industrial service are based on the inadequate measuring probe principle, while other known infrared measuring devices meet laboratory requirements only.

The problem which arises in the case of the standard continuous drier and its operation, therefore, is to control the drying process in accordance with the concentrations of evaporating matter and in conjunction with the burner control system. Furthermore, the determination of these concentration values should be characterized by a quick response and must be equally suitable for each of the volatile constituents encountered.

SUMMARY OF THE INVENTION

A solution to this problem is provided by a continuous drier for drying the printed webs of rotary web offset printing presses which has a drier section to apply a heated auxiliary gas—preferably an air current—to the web which is travelling in a web channel and is equipped with actuators for controlling the heater operation, flow rates and fresh air supply (the actuators being designed for connection to a control system), including the attendant transducers for the air current which is composed of fresh air, recirculated air and exhaust air. The drier also is equipped with actuators outside the drier for control of the ink and damping solution conditions, as well as the web speed and cleaning solution, and possesses at least one gas warning device calibrated to an upper gas/vapor concentration limit derived from carbohydrates. A beam path is provided in the air current between an IR radiation source and an IR receiver. The beam path exhibits a plurality of optical elements and functions as a measuring system. A measuring and evaluation circuit can be used to quantify, on the basis of a received intensity curve, the intensity of certain bands or sets of bands which can be attributed to certain gas/vapor components. The band intensity values can be standardized by means of a quantitative evaluation process such as the baseline method, thus yielding comparable relative transmittance or extinction values. The intensities of the specific bands which are continuously measured "on line" can be compared to a chosen, preselectable extinction value. There is provided a control system with a predefinable extinction control characteristic according to the gas/vapor concentration of the specific gases/vapors and the final controlling elements can be actuated according to a comparison between the set point and the actual value of the existing gas/vapor concentration to be controlled.

Further solutions regard the operation of the drier in the course of the normal printing run and during the cylinder cleaning cycle, the latter being carried out with the web running. The band intensities of the specific gases can be continuously quantified on line during the printing run and the cylinder cleaning cycle. The actual extinction values corresponding to the gas/vapor concentration are changed towards an extinction or concentration set point, respectively, by actuating the controlling elements, said set point value being kept below the upper limit. A reference variable characteristic for the printing run is based on the extinction corresponding to the gas/vapor concentration of at least one liquid constituent (vehicle) of the ink. Another reference variable characteristic for the blanket cleaning cycle is based on the extinction corresponding to the gas/vapor concentration of at least one of the cleaning agent components, particularly naphta. The control device is designed to implement either one or the other reference variable characteristic.

In another embodiment, the invention is applied to the operation of a continuous drier in which the drying atmosphere in the drier can be heated by open combustion of a fuel gas in a burner. The intensities of the specific bands or sets of bands can be quantified for at least one constituent (e.g. $CH_4$) of the fuel gas and/or for at least one constituent of the exhaust gas (e.g. CO). The intensities can be represented as relative transmittance or extinction levels according to a known quantitative evaluation process. The combustion can be controlled, on the basis of the extinction values, as a function of the burner setting and temperature, as well as the drier actuator settings, in an attempt to achieve complete combustion, i.e. a combustion without fuel gas residue and CO. The actuators of the burner are operable by a control system processing the extinction value input.

In another embodiment, the invention is applied to a drier's operation during the normal printing run. The IR measuring beam path permits an on-line quantification of the bands or sets of bands of liquid constituents (vehicle) of the printing ink. These intensities can be expressed in terms of the relative transmittance or extinction using a known analytical method. The continuously measured band intensities or extinction values can be compared to preselected or stored values. Any deviations in the concentrations o the vehicle constituents from the reference values, as reflected by the extinction values, can be identified and recorded. The drier operating conditions can be adapted according to the evaporation of the other ink constituents by the control device through modification of the burner actuator settings, damper positions and rotational speeds of the flow and fresh air supply systems.

The advantages of the invention are as follows:

The gas or vapor measurement by infrared absorption works without supplementary gas supply as in the case of FID. The beam path for the absorption measurement is simple to establish because all it requires is a transmission of radiation through the gaseous or vaporous atmosphere at any appropriate place in the continuous drier. Suitable locations are available in the existing flow paths or channels. The beam path can even be established near the heating system or, in the case of an unprotected heating unit of the gas burner type, near the circulating air with its high content of combustion gases. The absorption caused by the fuel and exhaust gases can be used as an input for the burner control system. The beam may even be passed through the flame itself.

The operation of the beam path is virtually unaffected by temperature influences. Any potential condensation of constituents which are likely to contaminate the mirrors or lenses can be prevented by heating the mirrors or lenses to a temperature beyond the condensation point. Alternatively, such contamination can be removed either automatically or manually from time to time.

The radiation intensity can be increased in a fairly simple manner by raising the temperature (and hence the output) to the point where the detection requirements will again be met.

In order to determine the liquid constituents evaporating from the ink, or from the washing solution during blanket cleaning, it is possible to perform an initial basic IR spectrometric identification of the major constituents involved (qualitative analysis or structure determination). The infrared spectrometer will in any case operate over a wide spectrum, i.e. the basic vibration range, by using a Fourier transformation. Once the essential constituents have been determined, the detection function of the system can then be limited to these constituents by mounting suitable filters for their corresponding absorption ranges in the beam path or by installing selectively operating detectors. This will permit a selective identification of the types and quantities of oils and resins added to harden the printing inks, as well as of ingredients such as the naphtha contained in the blanket cleaning solvent. A simple IR measuring system will thus operate with several "windows" corresponding to the number of constituents and each representing a suitably narrow band; these windows may also be implemented in the form of detectors having a specific reception range.

Beam guidance can basically be provided by means of mirrors or lenses. Standard, plane or spherical mirrors providing convergent light focussing are simpler than lenses and may be made of materials such as metal. A division of the beam into an undeflected and a deflected beam portion can be achieved by devices such as a semipermeable mirror. The beam guidance system may also rely on movable filters, mirrors and screens.

For the quantitative evaluation, the intensity of the characteristic band of the substance concerned (which appears attenuated as a result of absorption) is compared with a similar and relatively constant intensity, which may be attenuated or not. The net maximum absorbance is obtained from the logarithm of this ratio, or from the differential of the logarithmized values, from a fixed base of fairly constant or maximum transmittance to the peak value of the key band.

As the band depth of the absorption wavelength increases logarithmically with the concentration and length of beam travel, it is possible to amplify the signal and improve the contrast between the background level and the absorption band by extending the beam path length; for this the beam path can be folded as in the case of a multiple passage through glass vessels.

In view of the fact that the radiation source and the radiation receiver are not exactly opposed, the return of the beam can be achieved by means of a retroreflector (a so-called "cat's eye" reflector) which is fairly insensitive when it comes to mechanical adjustment requirements. Such a reflector returns the beam in a parallel direction with a minimum of offset.

Generally, the optical elements necessary to implement the IR beam path can be arranged within the continuous drier. In this case, however, they will be exposed to the contaminating vaporous atmosphere, temperature changes and heat-induced deformation and stress. Once the infrared spectral region selected for the measurement has been selected (preferably medium infrared (MIR) with a wave number between 4000 and 400), it is necessary to modify the drier design by installing suitable windows in such a way that the hot drier is hermetically sealed off while still allowing the passage of an optical beam, thus allowing sensitive optical components to be mounted externally in an accessible and reliable way. The windows which are translucent to broadband radiation are flange-mounted so as to be easily accessible. To avoid an accumulation of condensed matter and flow-induced contamination streaks, the windows should in each case be mounted in a suitable location of the drier which exhibits fairly homogeneous flow and heat conditions. The optical elements requiring supports are mounted on rugged brackets. In addition to the IR radiation source, it is possible to provide another light source which is subject to the same adjustment conditions and emits its radiation to a receiver matrix that will indicate deviations from the desired beam path and, based on these deviations, will actuate an automatic correction of the optical elements which returns them to their desired position.

The printing inks, which contain approx. 10 to 30% of pigments dispersed in 60% to 70% of the vehicle, are marked by a characteristic IR spectrum which is a result of their mineral oil, plant oil and resin contents. The composition of the ink will vary throughout the printing process and with differing requirements. The bands or sets of bands corresponding to the vehicle constituents which evaporate in the drier in any significant amount may either be of the typical, identifiable and catalogued type, or else appear as unidentifiable or barely identifiable absorption patterns. Regardless of this fact, the individual spectrogram of a given ink will exhibit unvarying band position and even unvarying band intensity characteristics. Changes in the material composition of the ink, which result in wastage phenomena (absorption of damping solution, ink penetration into the paper, plaiting of web exhibiting poor drying properties, build-up, etc.), can thus be detected on the basis Of the detailed spectral composition. The band intensity, which reflects the concentration of an ink constituent in the vapor phase, will provide information on its volume percentage and the evaporation kinetics, so that the spectral values can supply interpretable and even analyzable data on the composition of the vehicle and the partial evaporation of constituents.

A certain typical spectrogram of a given ink can be compared with another spectrogram allegedly produced by the same ink, or with the spectrogram of another ink. In an exemplary embodiment, the evaluation unit mounted downstream of the radiation receiver may use autocorrelative methods.

The combustion process used to generate the hot air can be controlled by examining the fuel gases (which should normally burn without residue) for a presence of incompletely combusted matter and by determining to what extent such matter is in turn being combusted. The fuel gas contains gaseous carbohydrates which can be identified in the IR absorption process. Their presence in the drier atmosphere requires an improved combustion control. Identified CO" fractions also show that stoichiometric combustion conditions are not achieved. In the recorded spectrums, the gaseous carbohydrate compounds in the fuel gas appear as specific bands which will not only provide information on the combustion process, but also allow the latter to be quantitated. Methane ($CH_4$), for instance, which is the smallest such molecule, will yield an unambiguously identifiable set of bands that can be used for assay purposes.

An evaluation with respect to a specific substance or set of bands can be carried out if the analysis is performed in comparison to a given substance that is either mounted in the measuring system by way of a reference sample, or taken into account through computation of the band or set of bands it produces. If the reference sample approach is selected, it is possible to install a sealed vessel containing the reference gas or reference gas mixture in the beam transmission path. Reference measurements can also be realized by means of a flow tube which is adapted to the beam path and through which a reference gas, inert gas, or tracer gas of known composition is then passed. At the high throughputs in the drier, the influence of this reference gas load is negligible.

In view of the usually highly variegated measuring spectrum, the only feasible way to concentrate on one or more major constituents of the total substances which are contained in the drier atmosphere and will appear in the IR spectrum is to evaluate the corresponding characteristic bands individually. In the most straightforward case they will be available in tabulated form; on the other hand, the key constituents of the inks and the cleaning solution as well as the fuel and exhaust gases can be individually processed in the following ways:

- separate representation of a given constituent with preparation of a calibration curve ranging from the extinction point to a given concentration;
- introduction of a substance of known concentration into the measuring beam during the normal operating conditions to produce a continuous defined absorption, with quantification being accomplished by means of a known nondispersive method using a measuring gas filter; and
- installation of a selective filter working on the level of the band (or set of bands) in question.

It goes without saying that a measuring process may also be implemented by introducing specimen quantities of the substance in question into the drier via the web. This will additionally give the user the opportunity to determine the transition behavior of the substance as a function of the drying parameters (the continuous dryer being considered as an open system) and other variables such as web speed, paper type, etc.

In stationary operating modes where few changes occur, it is also possible to compare individual band intensities with the total carbohydrate measurements coming from FID measuring points.

The registered on-line measurements obtained with the IR absorption process should be recorded and stored, so that current operating conditions (ink, liquid blanket and burner cleaning agents) can be compared to reference data or specified target data.

Whereas a conventional continuous drier could only be operated in a stationary mode with respect to certain operating systems, and with fixed parameter settings in order to avoid hazards due to arbitrary changes, the operation of a drier with gas and vapor concentration measurement and the control of its inflammable atmosphere can now be designed in a more flexible way.

In the case of several drier sections with individually preset drier section outputs in the direction of the web, it is now possible to measure the concentrations between sections and provide a selective control of the drying sequence by acting on the temperature and flow conditions.

In addition, the IR absorption measurement is not susceptible to cross-sensitivities in the case of carbohydrates with oxygen bonding, CO or $CO_2$, which place a restriction on the use of the FID system.

The beam path can be adjusted in a large variety of ways by means of pivotable or insertable optical elements (mirrors, filters, cells) to meet individual requirements. Bands attributable to water, which are due to the water vapors of the normal ambient air and additionally indicate an evaporation of water from the web and the damping solution (including water vapor from the combusted fuel gas), can be used to establish a water balance because the intensities observed will exhibit differences depending on preset process conditions. Among the identifiable differences in process conditions, the user can distinguish whether the web runs with or without printing action, slow or fast, with low or high dot densities, low or high drier temperatures, or low/high flow rates of fuel gas, fresh air, exhaust air and recirculated air.

Due to the large number of light absorbing or reflecting surfaces in the drier, the IR radiation will be partly diffuse and attenuated by losses. In addition, the IR spectrometer will show cross-influences inherent in the hardware design so that all measured value curves must be related to the actual zero intensity at the given point. This zero intensity has to be individually obtained or defined at certain intervals in the sequence.

At the end of the continuous printing process and the start of the blanket cleaning cycle (as well as upon restart of the press run and at the end of the cleaning cycle), the system will show corresponding increases or decreases in band intensities in accordance with the carbohydrate constituents contained in the ink and cleaning solution.

BRIEF DESCRIPTION OF THE DRAWINGS

An embodiment of the invention is illustrated by way of example in the accompanying drawings, in which

FIG. 3 shows a schematic longitudinal section of a continuous drier;

FIG. 4A shows a schematic view of an FTIR spectrometer;

FIG. 4B shows the simplified beam path of a measuring beam apparatus using a nondispersive scanning process;

FIG. 5 shows the beam passage through the wall of the continuous drier:
a) beam with retroreflection through a window in a tube;
b) beam passage with beam deflection through windows;
c) beam passage with retroreflection using a stationary retroreflector;

FIG. 7B shows the band intensity analysis by means of the baseline method.

DETAILED DESCRIPTION

Figure 1:
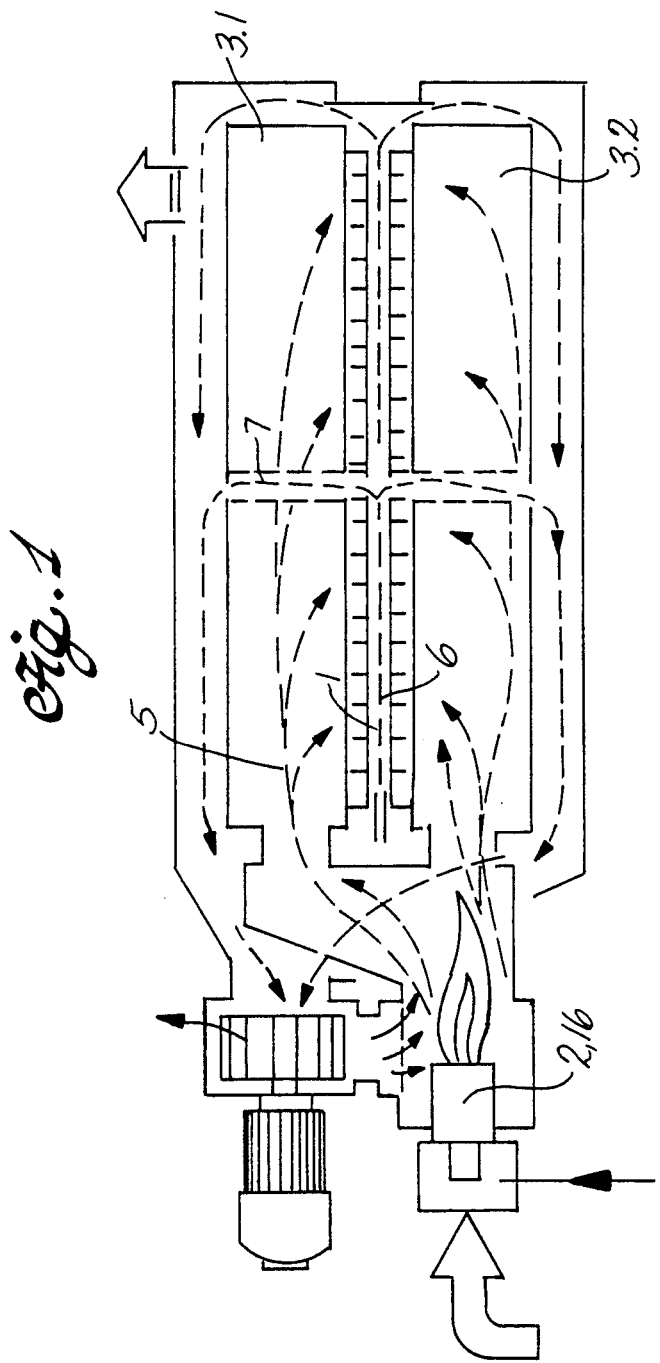
FIG. 1 shows a schematic sectional view of a continuous drier.

According to FIG. 1, the continuous drier for a web printed on the face and obverse sides consists of a heating system 2 operating as an air heater, an upper nozzle box 3.1, a lower nozzle box 3.2, and an air recirculation system 4. The air supply and exhaust air flows are marked with flow indicating arrows. As indicated by the simplified flow line arrows 5, the recirculation air flow in the drier is passed, after pre-heating, through the nozzle boxes 3.1, 3.2 towards the web channel 6 where it comes into contact with the face and obverse sides of the running web before it flows back to the heating system 2, now enriched with constituents of the ink and cleaning solution which have evaporated from the web 1. The stationary gas and vapor concentration in the continuous drier is controlled via the air supply and exhaust air flows because the volume flow of the ink will vary according to the printed areas, ink densities, and web speed. For regulation of the air supply and exhaust air flows, the attendant turbomachines or fans 17, 18 are controllable and additional dampers can be actuated.

The uniformity of the flow, and hence of the gas and vapor concentrations, is greatly dependent on the flow path design. Vapor, as used herein, refers both to particles suspended in gases and to compounds and elements in gaseous form. In order to shorten the return flow paths, which will reduce the flow losses, the nozzle boxes 3.1, 3.2 are equipped with cutouts 7 located approximately in the center of said nozzle boxes when viewed in the transverse direction x. These cutouts allow a flow and a partial inner circuit in the z-direction. The main axis of the cutouts 7 runs in the longitudinal y-direction.

The beam apparatus 11 for the IR measurement is provided at locations whose cross section permits a free beam passage and where volume elements of essential gas and vapor concentrations can be found in the flow.

Despite the "agitator vessel" characteristics of the drier, this gas/vapor concentration is not evenly distributed because of major flow intermixing phenomena. Points of maximum partial concentrations are located near the evaporation sources, i.e., next to the web 1 and, for the combustion process, next to the burner 16. Considered in the longitudinal y-direction, the concentration follows a rising curve which reflects the increasing temperature of the web once it has passed the drier inlet slot. Together with this temperature, but also in relation to the vapor travelling to the boundary surface of the paper and to the ink on the web, there is a simultaneous increase in evaporation rates. Average concentration values will appear at flow points which lack a gas or vapor source, e.g., upstream and downstream of the air recirculation system 4 and in the exhaust stack 8. The concentration characteristic is also reflected in the leakage air at the web inlet and outlet slots 9, 10.

The beam transmission apparatus 11 with its radiation source 11.1 and receiver or detector 11.2 may pass the drier in any direction.

Figure 2A:
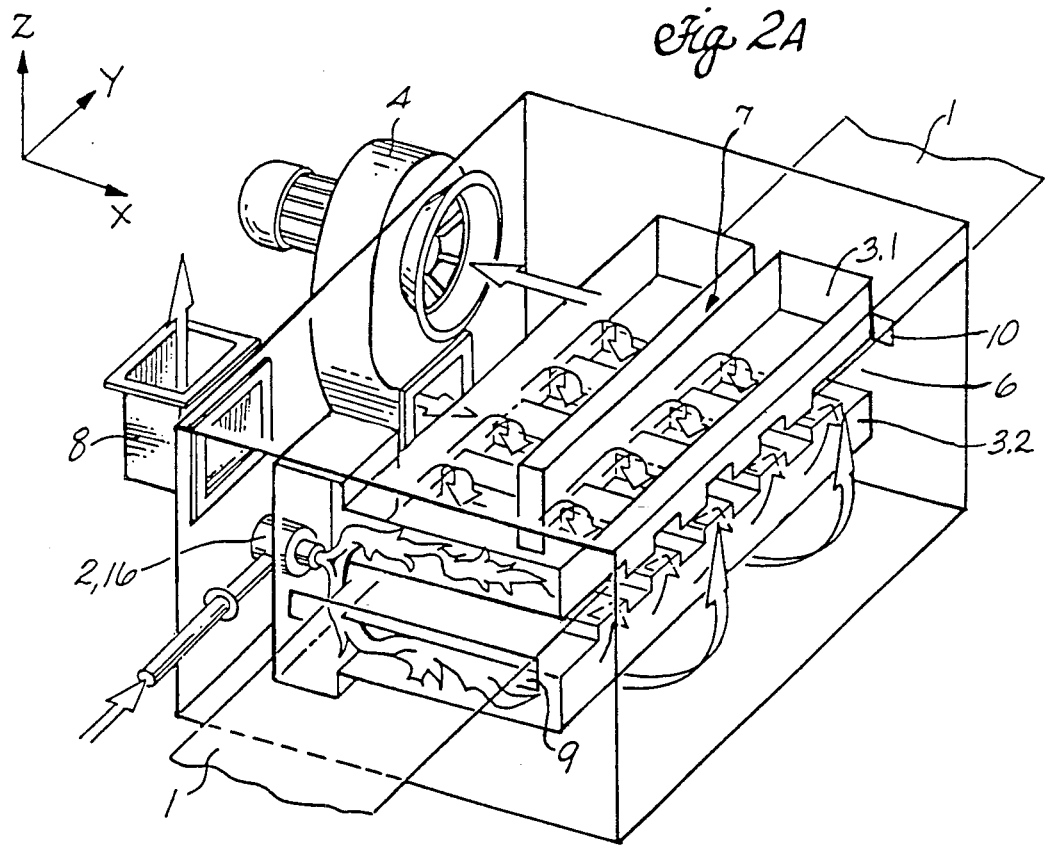
FIG. 2A shows a schematic three-dimensional view of a continuous drier.
Figure 2B:
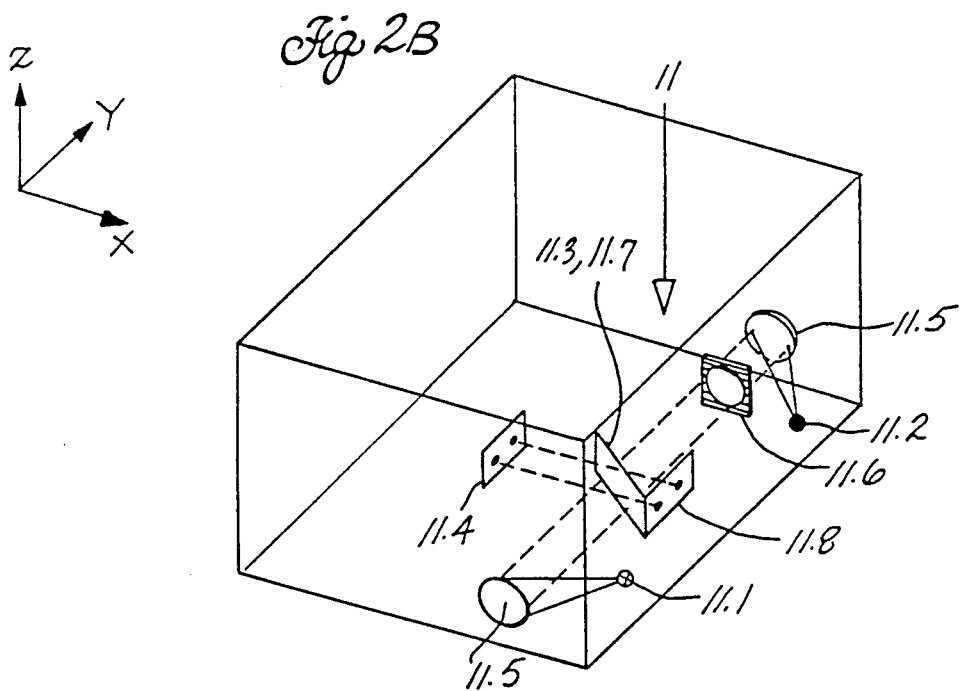
FIG. 2B shows a three-dimensional geometric representation of the continuous drier, complete with IR radiation apparatus and beam path.

FIG. 2B shows a beam transmission apparatus 11 with the main beam running in the y-direction. In this layout, the partial concentration values appearing in the volume elements passing the beam are integrated from the coordinate point y1 of the radiation source 11.1 through to the coordinate point y2 of the receiver 11.2.

A superimposition of the IR absorption in the y-direction over that existing in the x-direction (i.e., the longitudinal and transverse directions in relation to the web) is obtained through installation of the deflecting mirror 11.3 which deflects the transverse auxiliary x-beam to the reflecting mirror 11.4 from where it returns to the y-path, again via the deflecting mirror 11.3.

The beam transmission apparatus 11 shown in FIG. 2B essentially shows the following details. The beam emitted from the radiation source 11.1 is passed to a spherical mirror 11.5 of a paraboloid or ellipsoid shape which reflects it in a direction parallel with the measuring path. The concentration of the parallel beam on the receiver is in turn effected with a concentrating spherical mirror 11.5. A reflecting mirror, preferably a retroreflector 11.6, which is mounted in the path of the measuring beam, directs the measuring beam back to the transmitter side so that the radiation source 11.1 and the receiver 11.2 are mounted next to each other or in a concentrical arrangement. From the hardware design viewpoint, the concentrical arrangement requires the objective to have a certain shape.

In cases where a portion of the beam is to be passed on further, the deflecting mirror 11.3 which can be moved into the beam path is in the form of a semi-translucent mirror 11.3 which allows a portion of the measuring beam to pass while deflecting the remaining portion into the beam path of the transverse auxiliary x-beam, the direction of which coincides with the deflection direction; from here the auxiliary beam returns to the semi-translucent mirror 11.7 via the reflecting mirror 11.4. The collecting mirror 11.8 reflects useful radiation. At the same time, the position of the collecting mirror shown in FIG. 2B indicates that the deflecting mirror 11.3 can be swung out of its active deflection position into an inactive position, which would cause the beam path running in the x-direction to become inactive as well so that no concentrations existing in the transverse x-direction across the web 1 would contribute to the beam attenuation.

To ensure a proper operation of the optical elements, which may be subject to contamination by condensed moisture, these optical elements can each be provided with small heating units to prevent such condensation. Their temperature setting should preferably be above the maximum operating temperature of the drier.

The system may also include cleaning elements to remove optical contamination causing nonsystematic measuring errors.

The measuring beam path shown in the radiation apparatus 11 runs in the y-direction, parallel with the web 1 or the edge of the web. Along the cutout 7 the measuring beam path is not influenced by web oscillation. The transverse measuring beam in the x-direction runs parallel with the edge of the nozzle boxes 3.1, 3.2 or between the nozzle strips of said nozzle boxes 3.1, 3.2 carrying the outlet orifices.

FIG. 3 shows a gas burner drier with an upstream pair of nozzle boxes 3.1, 3.2 and a downstream pair of nozzle boxes 3.1, 3.2. The web 1 in this case is exposed to two drying air currents. Between the two sections, the air enriched with vapors is led away via the exhaust air stack 8.

Information on the formation of ink vapors and cleaning solution vapors can be obtained if the distribution of their concentration is measured at several points and across several measuring paths. To this end, there is disposed a first measuring path 12.1 on the level of the first pair of nozzle boxes 3.1, 3.2. A second measuring path 12.2 covers the second pair of nozzle boxes 3.1, 3.2. On the hardware level, these measuring paths 12.1, 12.2 are coupled by swivelling or inserting mirrors (e.g., retroreflectors, also knows as "cat's eyes") into the beam path extending through the drier to obtain shorter or longer transmission sections.

The beam path splitting principle, which separates the beam into a main beam path and an auxiliary beam path and works with only one transmitter 11.1 and one receiver 11.2, is illustrated in FIG. 2B.

The function of the measuring path 12.3 is to record the transmittance of the exhaust gas, which summarily contains all gases and vapors. As the gas constituent volumes circulating in the drier may dwell in the system for shorter or longer periods of time, the average dwell time of the gas constituents found in the exhaust stack represent a maximum value. The measuring path 12.3 will therefore not provide measurements of quickly released gases and vapors. In view of its compact design and its potential for a "total balance" measurement, however, it represents a particularly favorable location.

The measuring path 12.4 is located in the flow downstream of the unprotected heating system, which in this case is the burner 16. Flow conditions at this location should be controlled via additional auxiliary devices to ensure reproducibility.

The installation of an FTIR spectrometer working on the dispersion principle and being equipped with an interferometer will ensure a discrimination of all absorbing constituents with the exception of inevitable band overlap. An illustration of the principle of such an FTIR spectrometer is given in FIG. 4A. A portion of the interferometer contains a mirror 13 with an advancing drive. The increasing and decreasing beam intensity of the interference maxima observed as a function of the mirror advance is processed by a computer. The beam intensity is resolved into its components according to Fourier analysis. Due to the spectrum obtained over the measurable IR range, all absorbing gas/vapor constituents are present in a form which permits their mutual discrimination. The specimen section 14 shown in FIGS. 4A and 4B corresponds to the measuring paths 12.1 through 12.4. The incoming beam "e" falls on the sample section 14 where the specific absorption occurs, and is then passed to the receiver 11.2 as an outgoing beam "a".

The nondispersive spectrometric apparatus shown in FIG. 4B concentrates on a certain wavelength by using a selective type of receiver 11.2 or by mounting a selection filter 11.10 in the beam path. For calibration, comparison and measuring purposes, it is also possible to introduce a reference gas (either the gas to be measured, such as the vapor of an essential carbohydrate contained in the blanket cleaning solution, or else a tracer gas) into the beam path or the beam transmission apparatus 11; also refer to the filter-type reference material 11.11.

The output signal of the receiver 11.2 shown in FIG. 4B is passed to a processor P which performs the evaluation. The output of this processor is fed into subsequent indication circuits, limit comparators and amplifier lines to the actuators of the drier, the cleaning beams and the emergency press shutoff circuit. The processor is also coupled to the management system performing the ink analysis on the basis of the ink vehicle carbohydrate vapors.

FIGS. 5A, 5B and 5C show an application of the beam path concept using the beams "e" and "a" in a volume element restricted by the drier design, i.e., a compartment formed by the walls of a tube or other vessel or duct section 15. As shown in FIG. 5A, the beams "e" and "a" are passed through the flanged-on windows 11.9 and via a retroreflector 11.6 which returns the beam "a" to the transmitter side, thus allowing the radiation source 11.1 and the radiation receiver 11.2 (i.e., the transmitter and receiver devices) to be combined into one unit. In FIG. 5B the optical bank leads to beam paths on either side on the system component 15. The deflection mirrors mounted on each side of this system component 15 are not in contact with the gases or vapors.

A loose flange of the window 11.9 is equipped with a heating device 19.

FIG. 5C shows an alternative embodiment to FIG. 5A, using a stationary retroreflector 11.6. This arrangement will prevent the retroreflector from changing its position due to heat and stress acting on the system component 15. The stability of the optical bank is thus retained.

Figure 6A:
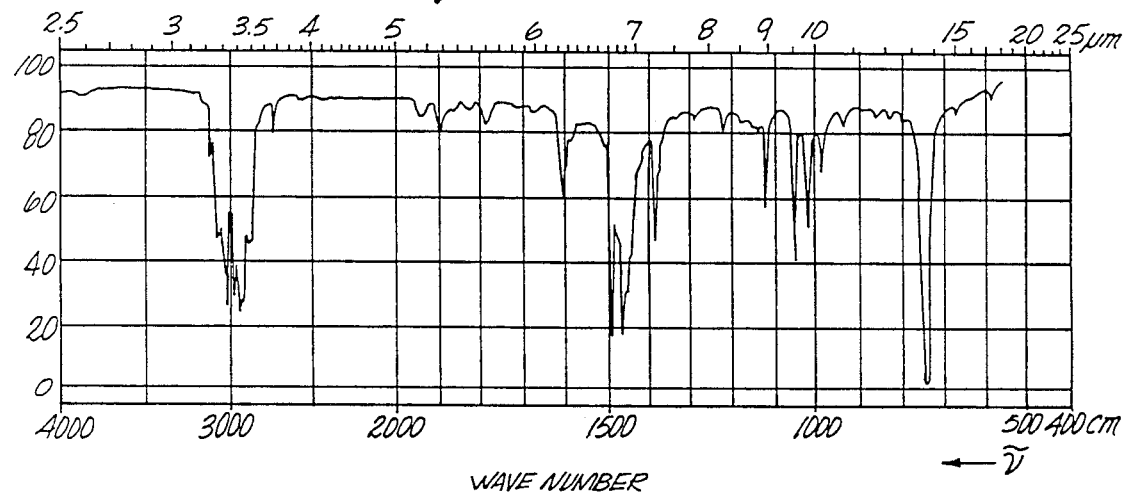
FIG. 6A shows an IR spectrum in which the linear wave number (on the X-axis) is plotted against the transmittance (on the Y-axis) for the MIR vibration range of any given carbohydrate.

Regardless of whether specific bands are examined and analyzed from a recorded spectrum (refer to FIG. 6A) or from a filtered, narrow-band spectral range, the key band exhibiting absorption loss must in each case be compared to an intensity of approximately constant value. A favorable method is to relate the band intensity in question to an absorption band of fairly constant level which can be clearly identified and is characterized by an isolated position. A reference intensity can also be defined by drawing a baseline through points of maximum transmittance (refer to FIG. 6B). The extinction proportional to the gas and vapor concentration can be calculated by way of approximation by applying the evaluation method based on the formation of baselines and using the logarithmized quotient $T_B/T'$. Even without numerical analysis, however, the band intensity will at all times provide an indication of whether the gas and vapor concentration in the drier process is growing or decreasing.

By using a suitable manual, mathematical (see notes on Fourier analysis) or optical selection process, the absorption spectrum permits an identification of all constituents or substances which lend themselves to IR identification at all. The CO band, for instance, which can be determined in a fairly unambiguous way, will indicate the degree of combustion in the burner 16. Other fuel gas identification bands show the extent to which the combustion is complete.

Whereas the FID measuring method will only yield an indication of the total carbohydrate contents, which in this method includes carbon oxides, the IR measuring apparatus for in-drier installation provided by the invention can distinguish between constituents resulting from the combustion process, the evaporation of printing ink, and the evaporation of cleaning solution.

Considering the dependence of the concentrations in the drier atmosphere and/or the gas/vapor phase from the drier operation parameter settings, the measured band intensities can be fed to the drier control system in unconditioned or analyzed form. As any change in concentration values achieved via the process technology will necessarily involve an intervention in the dosage (i.e., the ink supply in the case of the ink conditions and the cleaning solution supply to the cleaning beam in the case of the blanket cleaning cycle), the measured band intensity is also used to derive a reference signal for the supply proportioning systems. Apart from an immediate dosage reduction in the case of an identified over-concentration (particularly of vapors posing an explosion hazard), possible countermeasures include a reduction of the concentration through increased fresh and recirculated air supplies, as well as a reduction in temperature.

Furthermore, the recorded band intensities and recorded positions of the press and drier actuators can be used to obtain presetting values for sequence control processes using repeat commands or similar features.

Variations and adaptations of the invention beyond those discussed above will be apparent to those skilled in the art. The applicant does not intend to limit the invention to the disclosed embodiments but only to the spirit and scope of the following claims.

What is claimed is:

1. A continuous printed web drier for use in rotary web offset printing presses comprising:
   (a) a housing through which a printed web passes, the housing having an intake gas flow into the housing, an exhaust gas flow out of the housing and a heater for heating the gas within the housing;
   (b) an ink and damping solution supply to the web, a cleaning solution supply to the web and means for driving the web to pass through the housing;

(c) actuators for controlling the heater, the intake gas flow and the exhaust gas flow;

(d) actuators for controlling an ink and damping solution supply, a cleaning solution supply and web speed;

(e) a plurality of optical elements for measuring the intensity of extinction bands attributable to vapor concentrations within the housing;

(f) a measuring and evaluation circuit for receiving the band intensity measurements obtained by the plurality of optical elements, standardizing the measurements and comparing them to predefined extinction values; and (g) a control system for controlling the actuators in response to the comparisons of the measuring and evaluation circuit in order to regulate the vapor concentrations in the housing.

2. The drier of claim 1 wherein the gas flow is an air current.

3. The drier of claim 1 wherein the optical elements continuously measure the extinction band intensities.

4. The drier of claim 1 wherein the optical elements define a measuring path, wherein the passing printed web is elongated in its direction of travel and wherein the measuring path is proximate the printed web and parallel to the printed web's axis of elongation.

5. The drier of claim 1 wherein the optical elements define a measuring path, wherein the passing printed web is elongated in its direction of travel and wherein the measuring path is proximate the printed web and transverse to the printed web's axis of elongation.

6. The drier of claim 1 wherein the optical elements define a measuring path, and wherein the measuring path is proximate to the heater.

7. The drier of claim 1 wherein the optical elements define a measuring path, and wherein the measuring path is at least partially within the exhaust gas flow.

8. The drier of claim 1 wherein the optical elements define a measuring path, wherein the housing comprises a gas recirculation system for generating a recirculating gas flow within the housing, and wherein the measuring path is at least partially within the recirculating gas flow.

9. The drier of claim 1 wherein the optical elements define a measuring path, wherein the housing comprises a nozzle box for directing gas from the heater to the printed web, and wherein the measuring path is at least partially within the nozzle box.

10. The drier of claim 1 comprising a second heater for heating an optical element.

11. The drier of claim 1 wherein the optical elements comprise a reflecting mirror.

12. The drier of claim 11 wherein the reflecting mirror comprises a retroreflector.

13. The drier of claim 1 wherein the optical elements comprise a semi-translucent mirror for splitting optical beams passing through the optical elements.

14. The drier of claim 1 wherein at least one of the optical elements is moveable.

15. The drier of claim 14 wherein the moveable optical elements are pivotable.

16. The drier of claim 14 wherein the moveable optical elements are slidable.

17. The drier of claim 1 wherein the optical elements comprise a discriminator for selectively discriminating optical wavelength ranges containing extinction bands.

18. The drier of claim 17 wherein the optical wave length ranges correspond to wave numbers between 4,000 and 400, inclusive.

19. The drier of claim 17 wherein the discriminator comprises a filter lens.

20. The drier of claim 17 wherein the discriminator comprises a receiver having a plurality of matrixed optical elements for alternately discriminating different optical wavelength ranges.

21. The drier of claim 1 wherein the control system controls the actuators to maintain the vapor concentrations to within predefined parameters and wherein the predefined parameters are variable to accommodate different drier cycles.

22. The drier of claim 21 wherein the drier cycles comprise a drying cycle and a cleaning cycle.

23. A method for operating a continuous drier of a web-fed rotary printing press having actuators for control of heating, intake gas flow and exhaust gas flow comprising:

(a) heating a printed web to vaporize the liquid constituent used to carry ink to the printed web;

(b) measuring the extinction band intensities attributable to the liquid constituent vapor;

(c) comparing the extinction band intensity measurements to preselected values; and (d) controlling the actuators in response to the comparison to maintain vapor concentrations within predefined parameters.

24. The method of claim 23 comprising identifying and recording the comparison results.

25. A method for operating a continuous drier of a web-fed rotary printing press having a housing in which the web is dried, a fuel gas combustion heater within the housing and actuators for controlling fuel combustion rate, intake gas flow into the housing and exhaust gas flow out of the housing comprising:

(a) measuring the intensity of extinction bands for a component gas of the heater combustion; and (b) controlling the actuators in response to the measurement to optimize combustion efficiency.

26. The method of claim 25 wherein the heater combustion component gas comprises a constituent of the fuel gas.

27. The method of claim 26 wherein the fuel gas comprises $CH_4$.

28. The method of claim 25 wherein the heater combustion component gas comprises a combustion product.

29. The method of claim 28 wherein the combustion product is CO.

30. The method of claim 25 wherein the step of controlling comprises controlling the actuators to minimize the concentration of unburned fuel gas vapor.

31. The method of claim 25 comprising measuring the heater temperature and controlling the actuators in response to both the temperature and band intensity measurements.

32. A method for operating a continuous drier of a web-fed rotary printing press having a drying cycle and a cleaning cycle during which the web continuously runs, the drier having actuators for controlling heating, intake gas flow and exhaust gas flow comprising (a) continuously measuring the extinction band intensities of vapors in the drier;

(b) comparing the band intensity measurements for a printing ink constituent to a first preselected value during the printing cycle;

(c) controlling the actuators during the printing cycle in response to the comparison to the first preselected value;
(d) comparing the band intensity measurements for a cleaning agent to a second preselected value during a cleaning cycle; and
(e) controlling the actuators during the cleaning cycle in response to the comparison to the second preselected value.

33. The method of claim 32 wherein the cleaning agent comprises naphtha.

* * * * *

UNITED STATES PATENT AND TRADEMARK OFFICE
CERTIFICATE OF CORRECTION

PATENT NO. : 5,060,572
DATED : October 29, 1991
INVENTOR(S) : FRANZ WAIZMANN

Figure 6B:
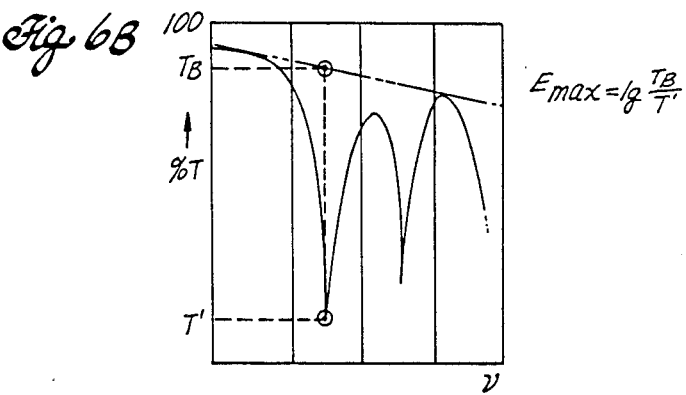

It is certified that error appears in the above-identified patent and that said Letters Patent is hereby corrected as shown below:

Col. 4, line 17, after "concentrations" "o" should read -- of --
Col. 8, line 42, "FIG. 7B" should read -- FIG. 6B --
Col. 8, line 46, after "web" insert -- 1 --

Signed and Sealed this

Eleventh Day of May, 1993

Attest:

MICHAEL K. KIRK

Attesting Officer

Acting Commissioner of Patents and Trademarks